United States Patent [19]

Ono et al.

[11] Patent Number: 5,394,499
[45] Date of Patent: Feb. 28, 1995

[54] OBSERVATION SYSTEM WITH AN ENDOSCOPE

[75] Inventors: Katsuya Ono; Masaru Shiraiwa, both of Tokyo, Japan

[73] Assignee: Olympus Optical Co., Ltd., Tokyo, Japan

[21] Appl. No.: 167,333

[22] Filed: Dec. 15, 1993

[30] Foreign Application Priority Data

Dec. 28, 1992 [JP] Japan .................................. 4-349449
May 11, 1993 [JP] Japan .................................. 5-109150

[51] Int. Cl.$^6$ .......................... G02B 6/06; A61B 1/06
[52] U.S. Cl. ........................ 385/119; 385/33; 385/115; 385/116; 385/117; 385/126; 128/4; 128/6
[58] Field of Search ............... 385/126, 127, 128, 115, 385/116, 117, 119, 33, 34; 128/4, 6; 356/241; 359/362, 379, 380, 381

[56] References Cited

U.S. PATENT DOCUMENTS

| | | | |
|---|---|---|---|
| 4,264,130 | 4/1981 | Ogura | 385/116 X |
| 4,331,380 | 5/1982 | Rees et al. | 385/116 X |
| 4,354,734 | 10/1982 | Nakahashi | 385/119 X |
| 4,425,025 | 1/1984 | Sunaga | 385/119 X |
| 4,523,806 | 6/1985 | Kojima et al. | 385/116 X |
| 4,571,022 | 2/1986 | Lama et al. | 385/116 X |
| 4,676,593 | 6/1987 | Adachi et al. | 385/119 X |
| 4,776,667 | 10/1988 | Yoshida et al. | 385/119 X |
| 4,788,967 | 12/1988 | Ueda | 128/6 |
| 4,824,205 | 4/1989 | Yamashita et al. | 385/119 X |
| 4,867,529 | 9/1989 | Utsumi et al. | 385/117 X |
| 4,964,692 | 10/1990 | Prescott | 385/117 X |
| 4,969,708 | 11/1990 | Leiner | 385/117 X |
| 5,036,834 | 8/1991 | Sugiyama et al. | 128/6 |
| 5,048,923 | 9/1991 | Tsumanuma et al. | 385/117 |
| 5,103,497 | 4/1992 | Hicks | 385/117 |
| 5,263,110 | 11/1993 | Anderson | 385/119 X |

OTHER PUBLICATIONS

T. Hosono; "Transmission Characteristics of Image Fiber"; 1983; pp.843-850; College of Science And Technology, Nihon University, Tokyo, Japan; vol. J66-C.

*Primary Examiner*—Brian Healy
*Attorney, Agent, or Firm*—Frishauf, Holtz, Goodman & Woodward

[57] ABSTRACT

An observation system for an endoscope has an entrance end face upon which an image is incident and an exit end face from which the image exits. The system comprises an image guide fiber of a very small diameter to allow transmission of the image, an object optical system arranged in front of the entrance end face of the image guide fiber, and a reproduction optical system arranged on the back side of the exit end face of the image guide fiber. The reproduction optical system is comprised of an eyepiece optical system and relay lens system. The maximal exit numerical aperture of the object optical system is greater than the maximal entrance numerical aperture of the reproduction optical system.

13 Claims, 18 Drawing Sheets

LP21 MODE

LP41 MODE

LP31 MODE

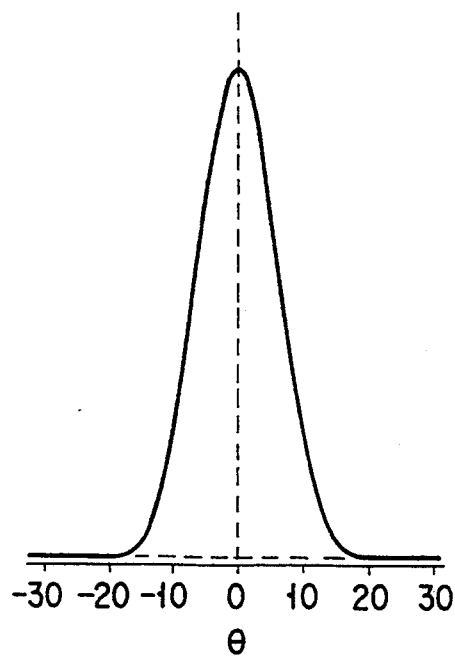
F I G. 4A
LP01 MODE
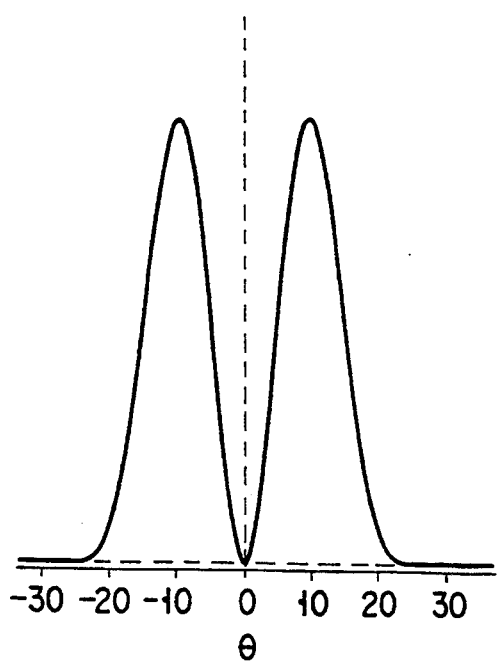
F I G. 4C
LP11 MODE
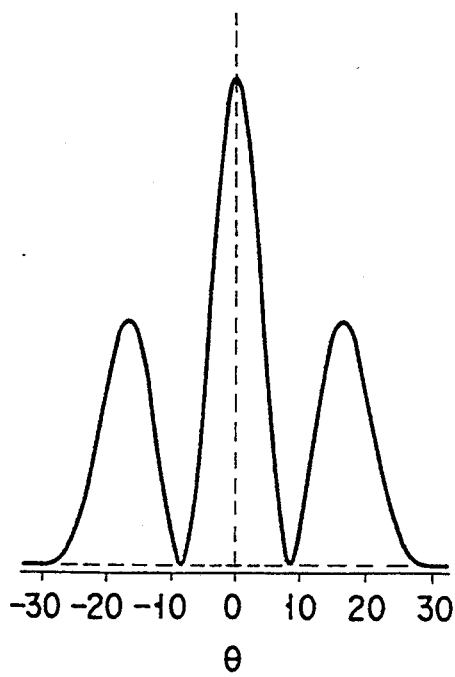
F I G. 4B
LP02 MODE
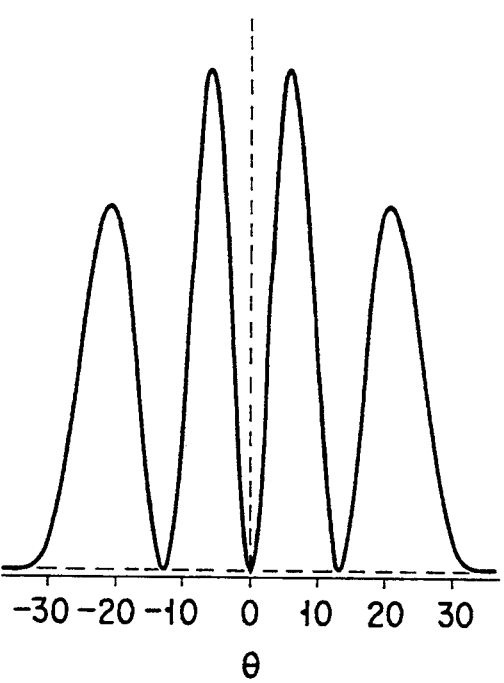
F I G. 4D
LP12 MODE

LP21 MODE

LP41 MODE

LP31 MODE

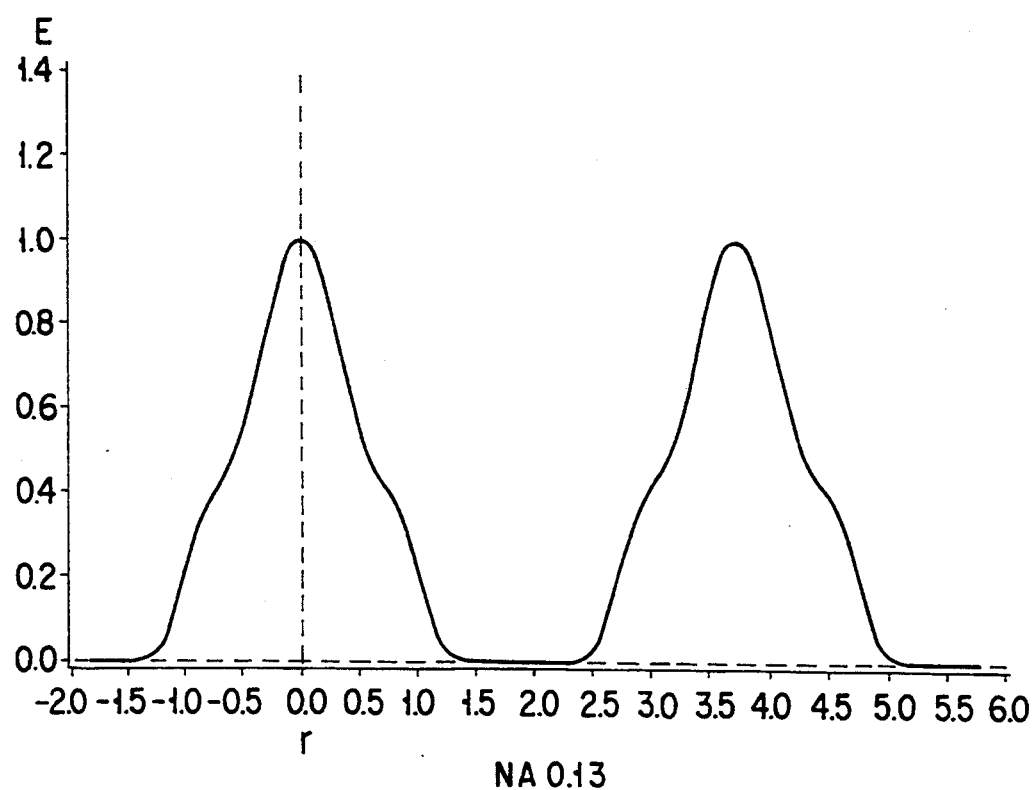
F I G. 5A
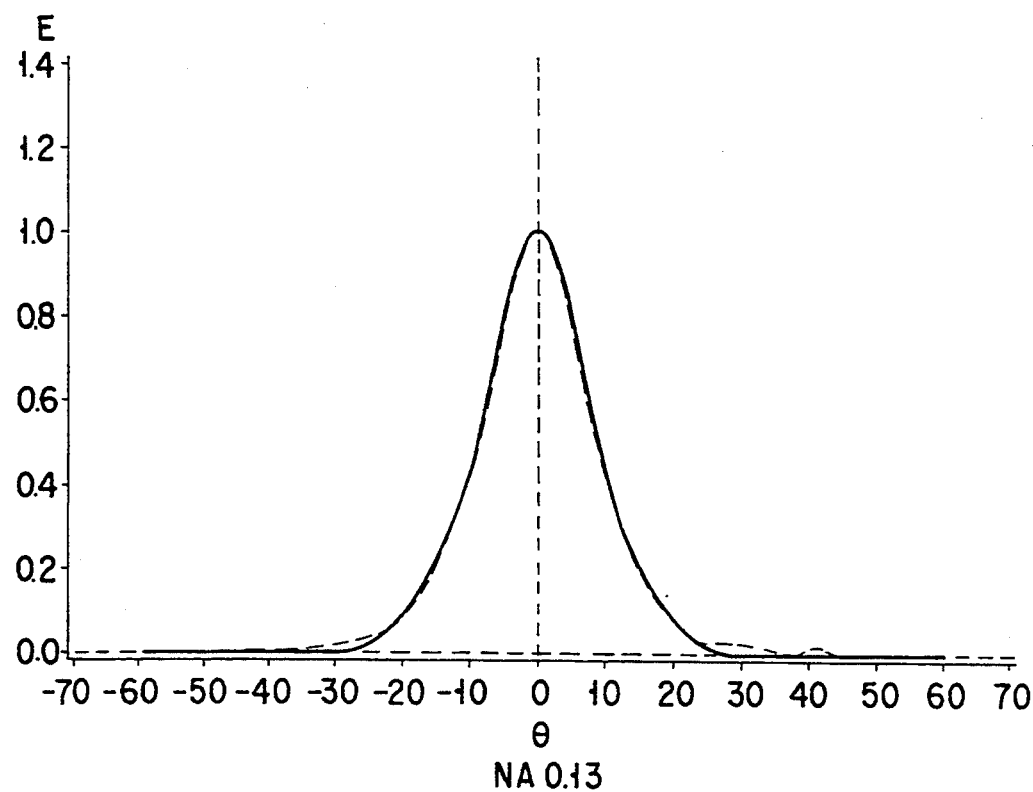
F I G. 6A

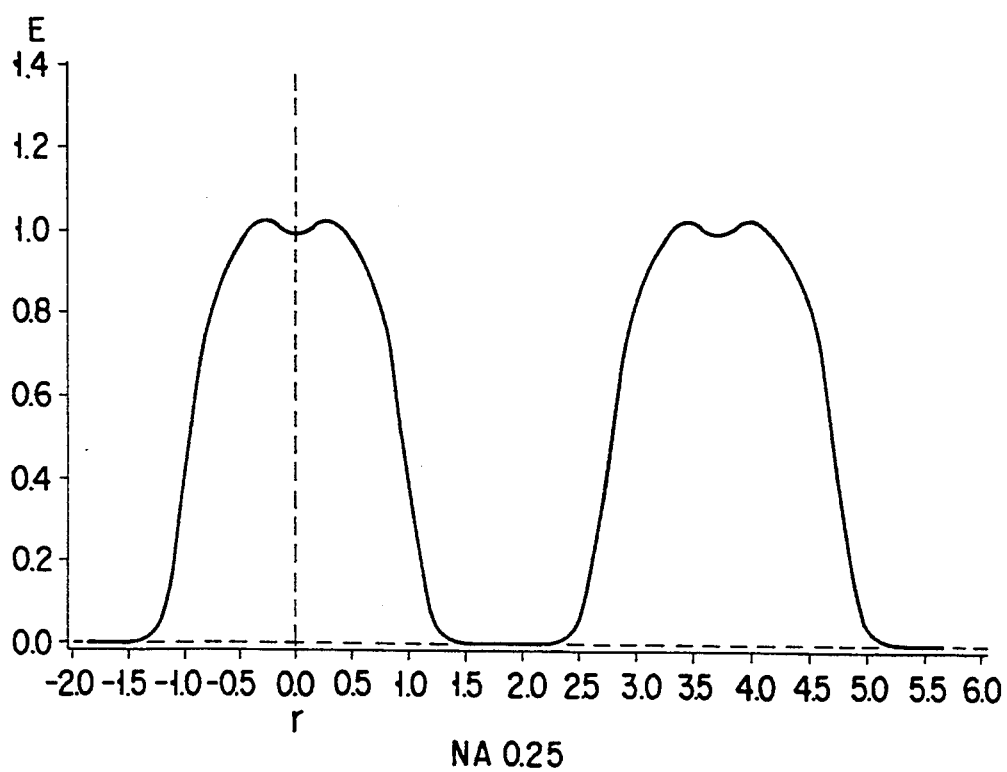
F I G. 5B
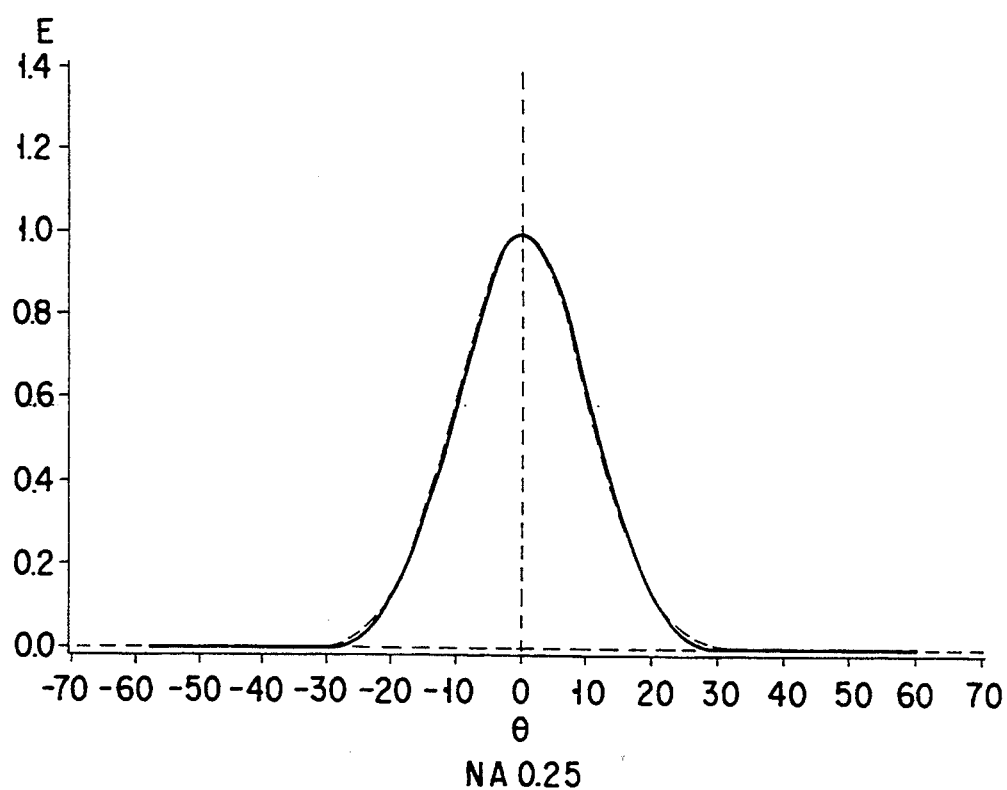
F I G. 6B

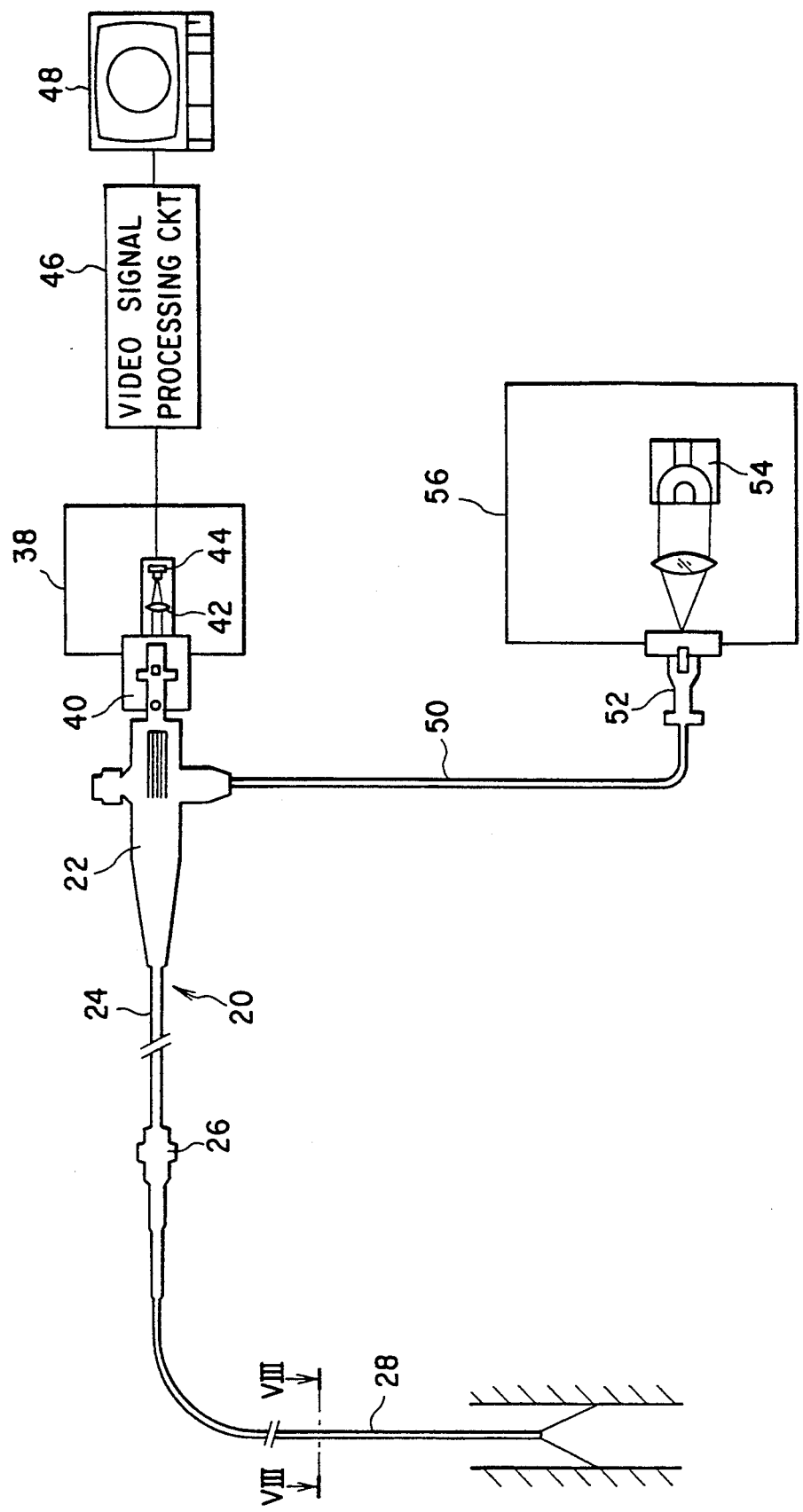
F I G. 7

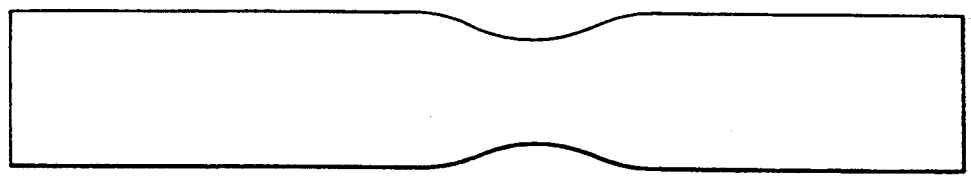
F I G. 19

OBSERVATION SYSTEM WITH AN ENDOSCOPE

BACKGROUND OF THE INVENTION

1. Field of the Invention

The present invention relates to an observation system with an endoscope having an image guide fiber of a very small diameter.

2. Description of the Related Art

An ordinary observation system using an endoscope comprises an image guide fiber for transmitting an image of a subject, an object lens for imaging a subject located at an entrance end face side of an image guide, and an eyepiece lens system for observing an image, as an amplified image, at an exit end face of the image guide or a relay lens system for directing the image at a light reception surface of, for example, a CCD, etc. The object lens has an F number of 2 to 4 and a numerical aperture (NA) of about 0.25 to 0.125 at the exit side, these being determined by a trade-off between the depth of field and the brightness of a lighting system. The eyepiece lens or the relay lens has an F number of 2 and a numerical number (NA) of about 0.25 at the entrance side.

Recently, practical use has been made of an endoscope for a blood vessel which includes an insertion section of a small diameter of the order of a few hundred of μm. In this type of endoscope, the brightness tends to be short due to the very small diameters of both an image guide and a light guide. Generally, for an optical system with a plurality of observation optical systems connected thereto, the brightness of the optical system is determined by the brightness of the lowest-illumination optical system.

In the optical system of this type, the numerical aperture (NA) at the exit side of the optical system located at the front side of an image guide for transmitting the subject image is made to correspond to the numerical aperture (NA) at the entrance side of the optical system located at the back side of the image guide. In a practical example, if the numerical aperture (NA) is 0.25 at the exit side of the object lens nearest the subject, the image guide is so designed as to be set to be over 0.25 and the numerical aperture is to be set to be 0.25 at the entrance side of the eyepiece lens or the relay lens. In this case, it has been common practice to impart a tolerance to the brightness of the back-side optical system, such as an image guide, eyepiece or relay lens, taking into consideration the assembly error, etc., of the optical system. In order to give more light to the optical system, it is necessary that the brightness levels of the respective optical systems be all increased.

For the small-diameter image guide it follows that a high amplification lens is necessarily employed as the eyepiece and relay lens. For this reason, the greater the numerical aperture at the entrance side of the eyepiece or the relay lens, much stricter the accuracy of component parts or accuracy of their assembly required.

Further, the image guide fiber comprises a common cladding and a great number of cores. Such an image fiber is manufactured in the following way. A greater number of relatively thick optical fibers called fiber elements are bundled and a resultant bundle, being heated, is spun into a fiber with a melted cladding set there.

It is desired that the image fiber be of a small diameter type. If, however, the core-to-core pitch (the center-to-center distance between the adjacent cores) is reduced below 10 μm, a cross-talk occurs due to the wavy nature of light, thus causing a marked degradation of a propagating image in the fiber.

A so-called "random image fiber" including various kinds of different-diameter cores has been known as an image fiber aimed at reducing a cross-talk, that is, a degradation in an image. However, this type of fiber becomes expensive due to the use of a plurality of kinds of optical fibers upon manufacture.

SUMMARY OF THE INVENTION

The object of the present invention is to provide an observation system for an endoscope having a very small-diameter image guide fiber which can make an observation under an adequate bright light condition without requiring any particularly strict component parts' accuracy and their assembly accuracy.

Another object of the present invention is to provide a low-cost image guide fiber of less cross-talk.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 4A–4G show luminous intensity distributions, on a luminous intensity distribution measuring plane, of various modes of of light;

FIGS. 5A–5D show a intensity distributions, that is, combined mode patterns, on exit end faces of various optical fibers of different numerical apertures, respectively;

FIGS. 6A–6D show intensity distributions, on a luminous intensity light measuring plane, of radiated lights from the exit end faces of the optical fibers of different numerical apertures, which correspond to FIGS. 5A–5D, respectively;

FIG. 7 shows an observation system according to an embodiment of the present invention which is equipped with an endoscope;

FIG. 19 shows an image guide fiber whose core diameter is partially narrowed.

DETAILED DESCRIPTION OF THE PREFERRED EMBODIMENTS

Figure 1:
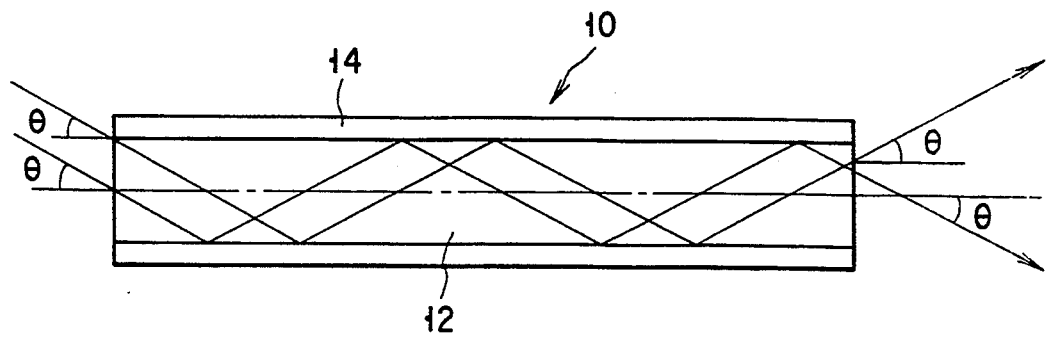
FIG. 1 shows a state in which light enters, passes through, and exits from, an optical fiber which can deal with transmission light opto-geometrically.

It has been known that, in general, the propagation of light can be optogeometrically treated in an optical fiber whose core diameter is adequately great to the wavelength of propagation light. Let it be assumed that, as shown in FIG. 1, an optical fiber 10 comprises a core 12 and a cladding 14. A light beam incident at an incident angle $\theta$ on the core 12 of the optical fiber 10 exits at the same angle $\theta$ from an exit end of the optical fiber. Since it is considered that, in the optical fiber 10 whose core diameter is enough great to a wavelength involved, the incident angle $\theta$ of the light beam is held even within the optical fiber, the numerical aperture (NA) at an entrance side of an eyepiece or relay lens is so designed as to be set equal to that at an exit side of an object lens.

For a so-called optical fiber whose core diameter is very small, that is, of the order of a few times the wavelength of propagating light, on the other hand, it is not appropriate to deal with the light opto-geometrically and it is necessary to treat it from the standpoint of wave optics. The optical fiber of a very small diameter allows propagation of only light of a specific guided mode satisfying an eigenvalue derived from the wave equation. The inherent intensity distribution corresponding to a mode called a "mode pattern" emerges on the exit end face of the optical fiber.

FIGS. 3A to 3G show intensity distributions (mode patterns) emerging on the exit end face of the optical fiber versus various guided modes. In these figures, the abscissa represents a radial distance $\gamma$ ($\mu$m) from the center of the core of the optical fiber and the ordinate represents a standardized intensity.

Figure 2:
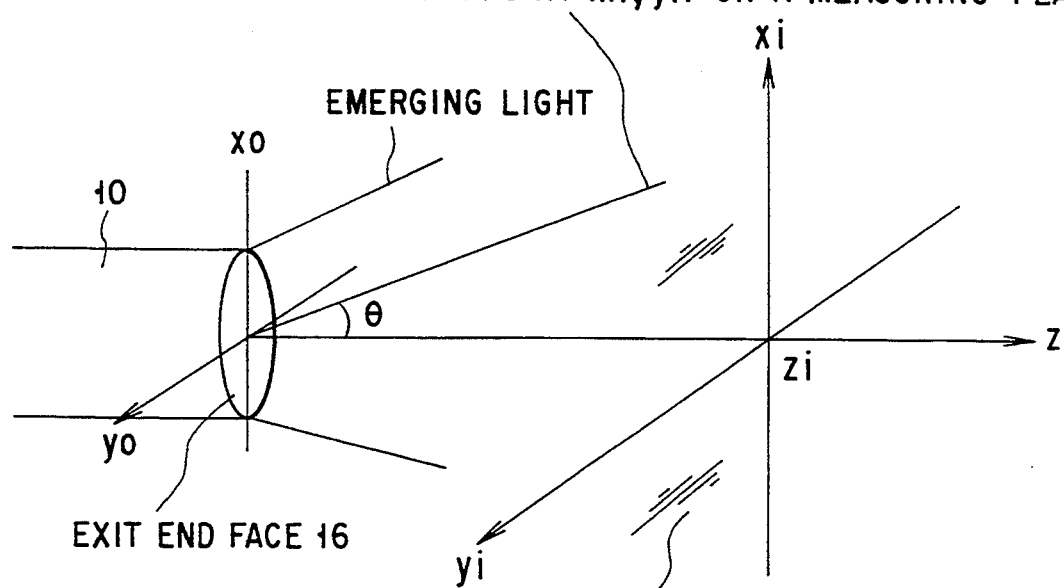
FIG. 2 shows a coordinate system, taking into consideration, a luminous intensity distribution, on the luminous intensity distribution measuring plane, of light which exits from an end face of an optical fiber.
Figure 3A:
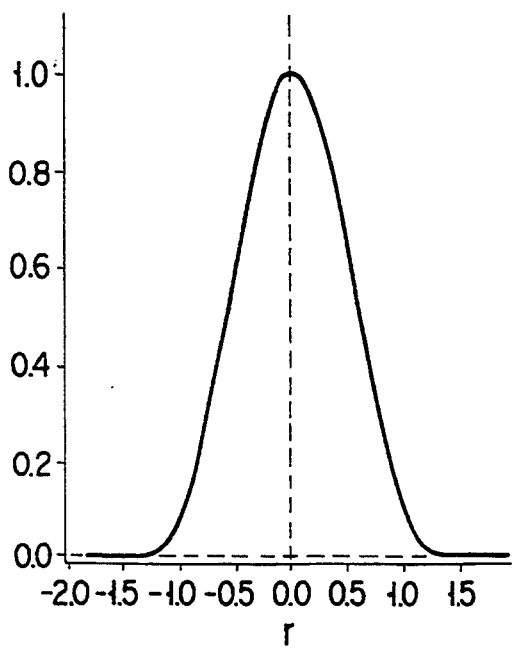
FIGS. 3A–3G show luminous intensity distributions, that is, mode patterns, on exit end faces of the optical fibers, of various modes of light, respectively.
Figure 3C:
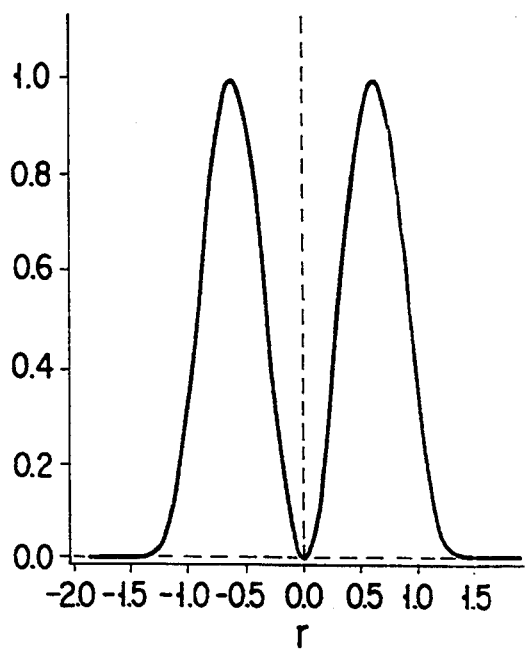
Figure 3B:
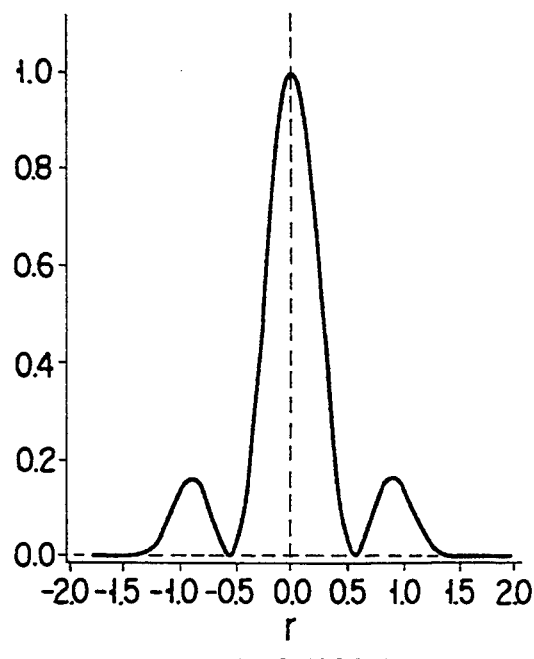
Figure 3D:
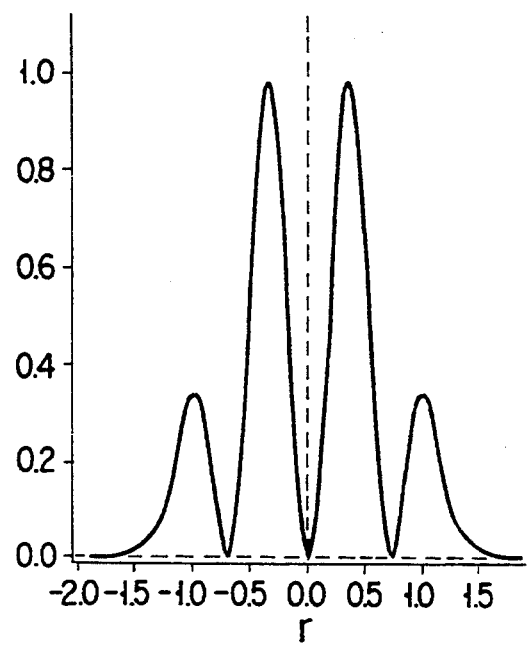
Figure 3E:
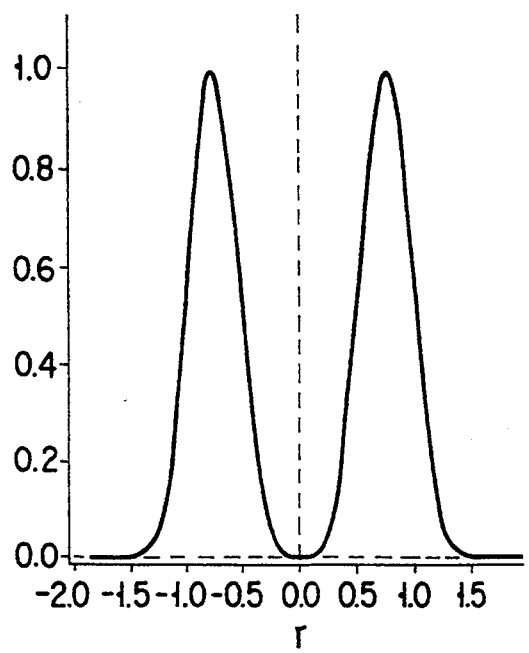
Figure 3G:
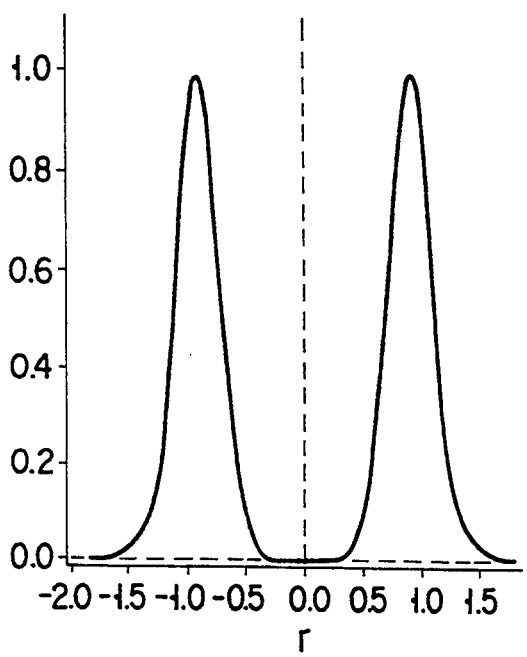
Figure 3F:
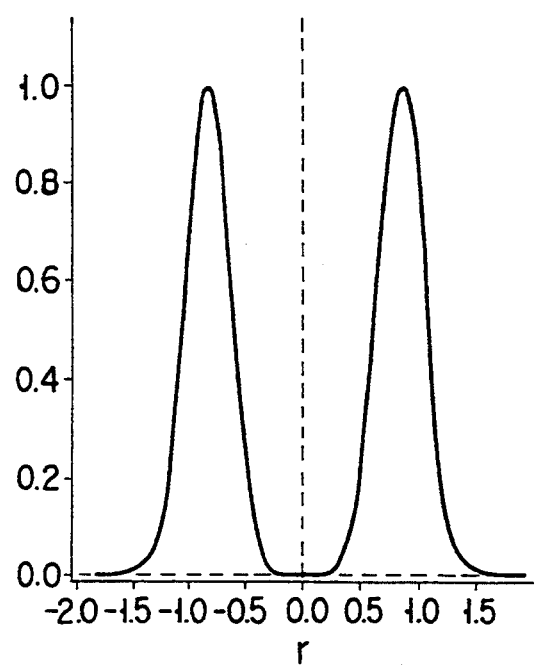
Figure 4E:
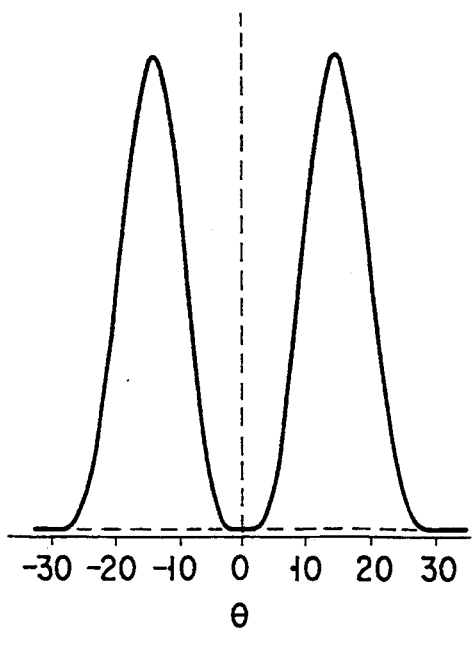
Figure 4F:
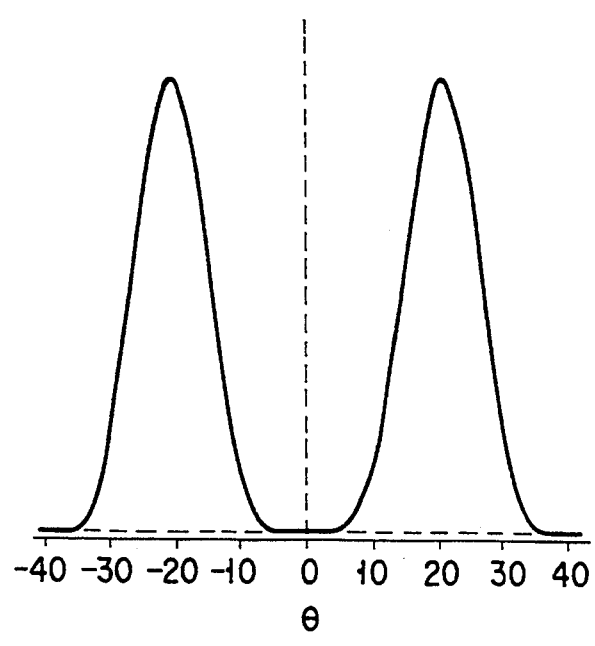
Figure 4G:
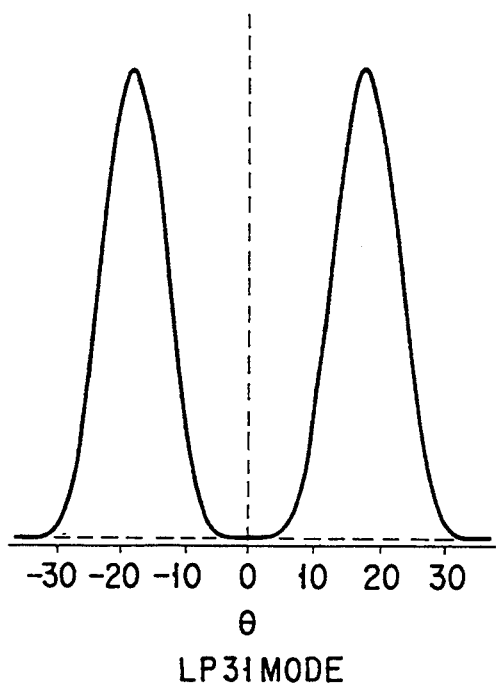
Figure 5C:
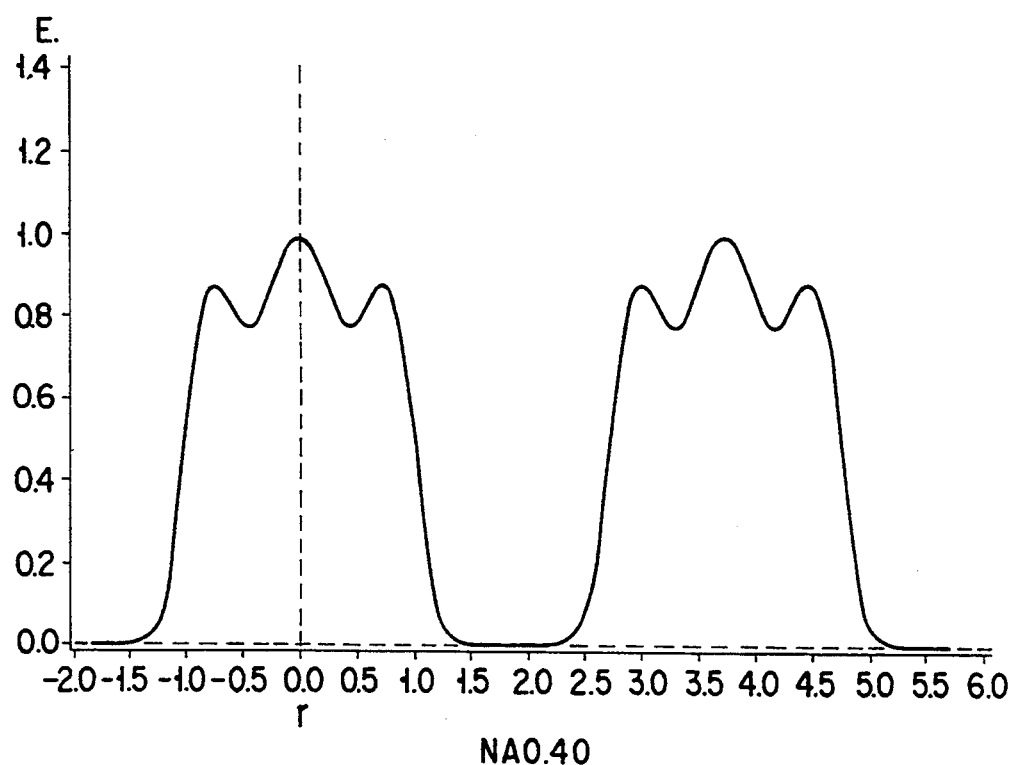
Figure 6C:
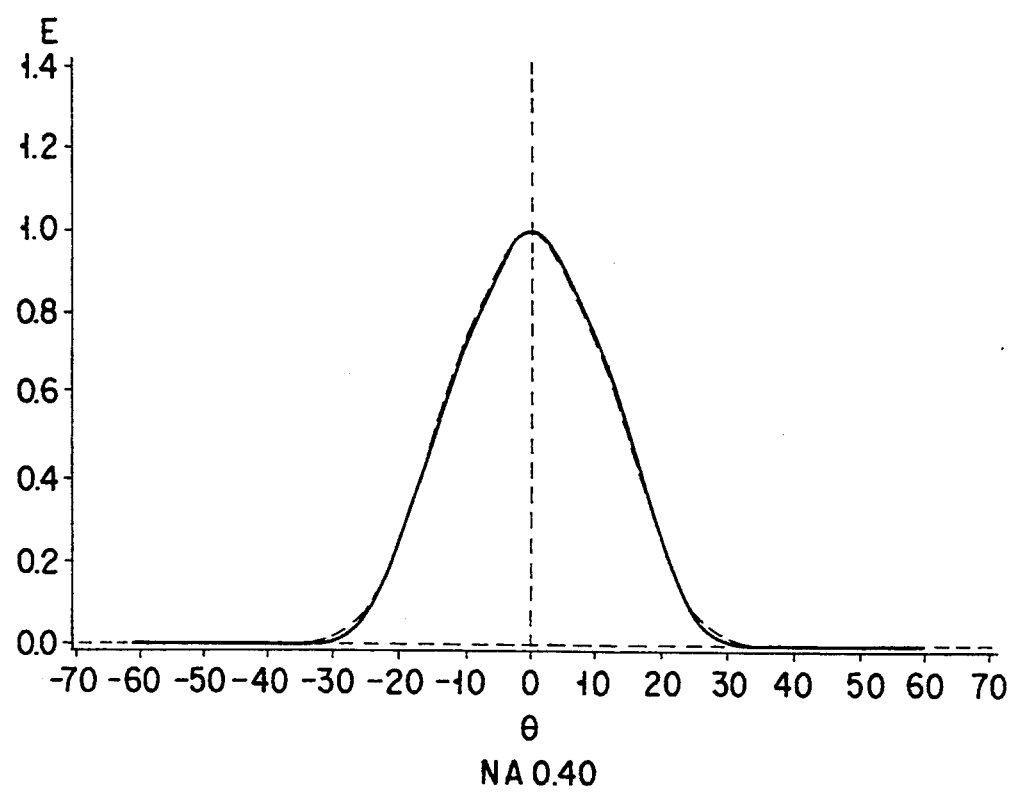
Figure 5D:
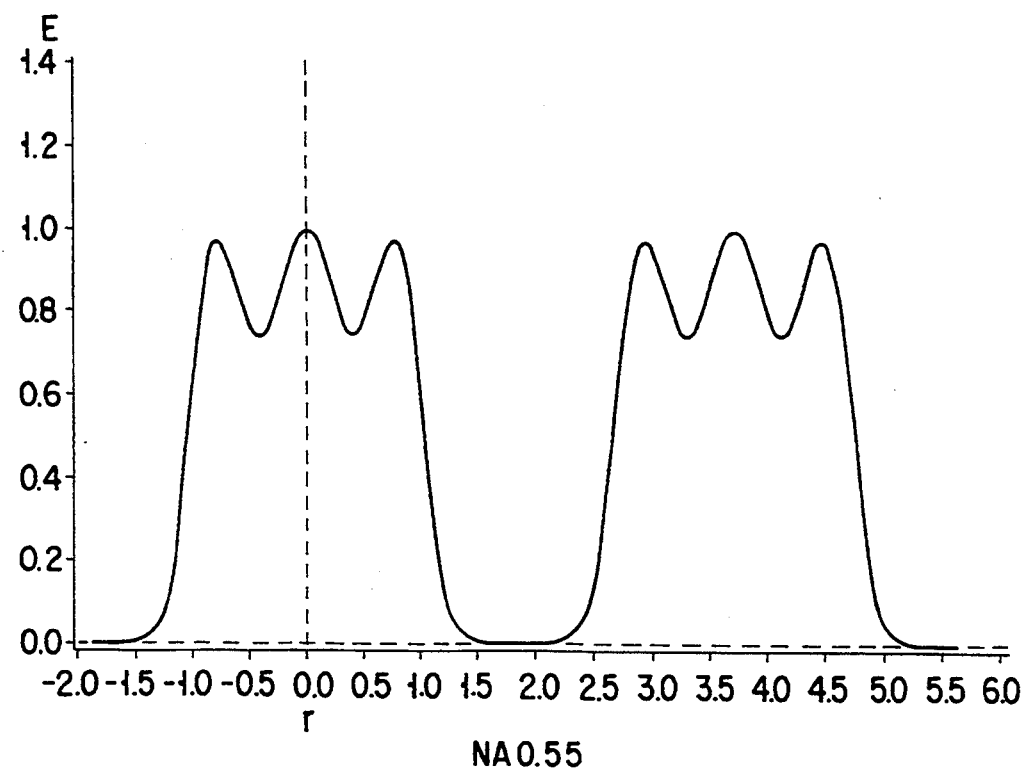
Figure 6D:
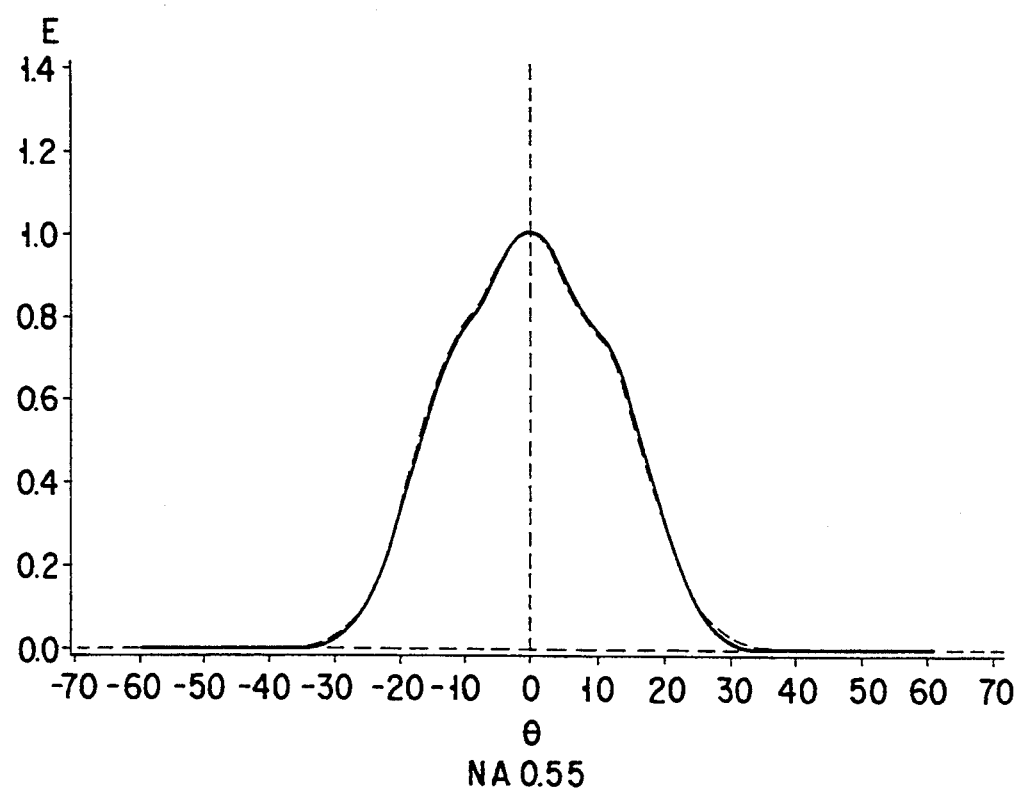

Now consideration will be given below about the coordinates system as shown in FIG. 2. The luminous intensity distribution (intensity) I, on the luminous intensity distribution measuring plane 18, of light emerging from the exit end face 16 of the optical fiber 10 is represented by a sum obtained through the Fraunhofer diffraction and it is given by the following equation:

$$u_n(x_i, y_i) = \Sigma a_n u_n^2(x_i, y_i) \quad (n: \text{an integer}) \quad (1)$$

$u_n(x_i, y_i)$ is given by $$u_n(x_i, y_i) = \frac{1}{j\lambda z_i} \exp\left[j\frac{2\pi}{\lambda}\left(z_i + \frac{x_i^2 + y_i^2}{2z_i}\right)\right]$$

$$\int\int_{-\infty}^{\infty} v_n(x_0, y_0)\exp\left[-j2\pi\left(\frac{x_i x_0 + y_i y_0}{\lambda z_i}\right)\right]dx_0 dy_0$$

where $v_n$: a function representing the amplitude of each mode on the exit end face 16 of the optical fiber;

$u_n$: the amplitude of each mode on the luminous intensity distribution measuring plane 18;

$a_n$: a coefficient representing the magnitude of the mode function; $\lambda$: the wavelength; $z_i$: the distance from the exit end face 16 of the optical fiber to the luminous intensity distribution measuring face 18;

$x_0, y_0$: the coordinates on the exit end face;

$x_i, y_i$: the coordinates on the luminous intensity distribution measuring plane 18; and n: a subscript representing a mode number.

FIGS. 4A to 4G show intensity distributions on the luminous intensity distribution measuring plane 18 versus the mode patterns as shown in FIGS. 3A to 3G. In these figures, the abscissa represents the exit angle $\theta$ and the coordinate, the standardized intensity.

In this connection it is to be noted that the light actually propagating in the optical fiber is composed of light of various modes. The ratio of the modes varies with a varying F number of the object lens or a varying numerical aperture. Correspondingly, the intensity distribution (a combined mode pattern) varies on the exit end face 16 of the optical fiber and on the luminous intensity distribution measuring plane 18.

FIGS. 5A to 5D, each, show an intensity distribution, that is, a combined mode pattern, on the exit end face of the optical fiber of a different numerical aperture. In these figures, the abscissa shows the radial distance $\gamma$($\mu$m) from the center of the core of the optical fiber and the ordinate, the standardized strength. Here, the intensity distribution of the adjacent optical fiber is also shown in these figures.

FIGS. 6A to 6D, each, show the intensity distribution on the luminous intensity distribution measuring plane versus each of the combined mode patterns of FIGS. 5A to 5D. The abscissa represents the exit angle $\theta$ and the ordinate, the standardized strength. In FIGS. 6A to 6D, the solid line and dotted line represent a calculated from Equation (1) and a measured value, respectively. As will be appreciated from each figure, both are substantially the same as each other. Given below is the specification on those image guide fibers measured and calculated.

the core diameter: 2.22 $\mu$m

NA: 0.51 the number of pixels: about 3,000 the length: 1.5 m the V value: 6.34 ($\lambda$=550 nm)

The brightness of the image obtained through the eyepiece and relay lens is a total amount of light passing through the inside of the aperture of the lens system above, meaning that, for the intensity distribution obtained from Equation (1), this is equal to an integrated one of a portion corresponding to the inside area of the aperture. That is, that is an amount of light in a range corresponding to the inside of the aperture (below 14.5°

, at the F number of 2). The greater the amount, the brighter the image.

For the optical fiber to be delt with opto-geometrically, the image does not become brighter even if the numerical aperture (NA) on the exit side of the object lens is made greater than a maximal numerical aperture (NA) on the entrance side of the eyepiece or relay lens. This is because, among that light passing through the aperture of the object lens, a light portion greater than the maximal aperture of the eyepiece all passes through the outside of the aperture of the eyepiece.

For the optical fiber having a small V value (for example, below 10) at the core diameter of a few $\mu$m, on the other hand, it has been known that the greater the numerical aperture, the greater the intensity of some mode (for example, a higher-order mode).

That is, upon examination for the luminous intensity distribution of each mode in such a type of optical fiber, the respective mode all has an intensity at an inside of the maximal aperture (for example, 14.5° if F number=2) of the eyepiece and it follows that, when the aperture of the object lens is set greater than the maximal aperture of the eyepiece, a brighter image is obtained.

Figure 10:
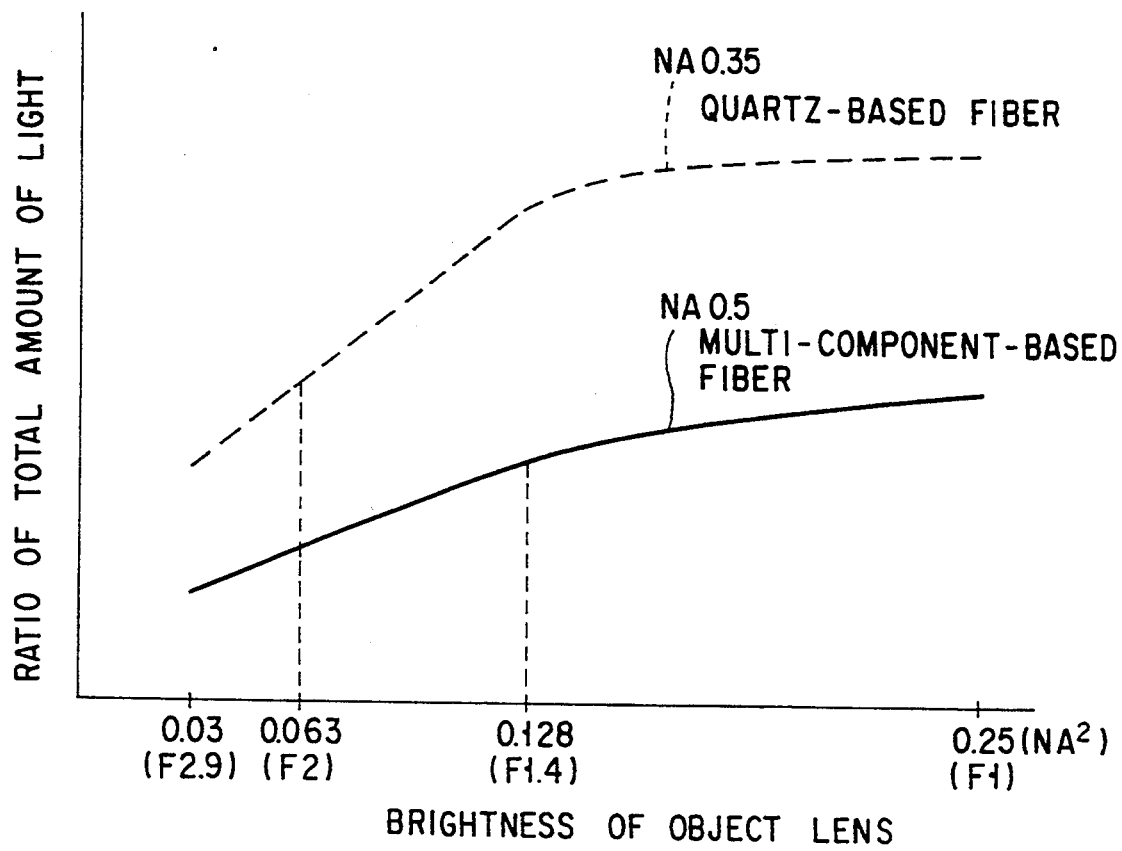
FIG. 10 shows a ratio of an F number of an object lens to a total amount of light at an exit side when an F number of an eyepiece is 2.

FIG. 10 shows a ratio for a total amount of light at the exit side of an image guide when both F number at the exit side of the image guide is fixed to "2" and F number of the object lens varies. From this it will be seen that, even if the object lens side becomes brighter than F number on the exit-side optical system, the amount of light is still increased. The brightness of an image obtained is increased when the aperture of the object lens is set to be greater than the maximal aperture of the eyepiece. This effect is particularly prominent for an optical fiber having a small V value (for example, below about 10).

Figure 8:
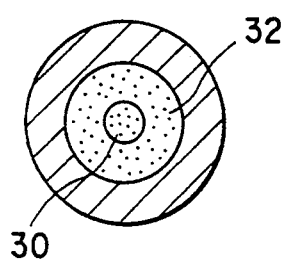
FIG. 8 is a cross-section, as taken along line VIII—VIII in FIG. 7, showing an insertion section shown in FIG. 7.

FIG. 7 shows a general arrangement of an endoscope system, according to the present invention, which is used for blood vessels. The endoscope 20 has an operation section 22, a flexible extension tube 24 connected to the operation section, a grasping section 26 provided at the forward end of the extension tube, and a flexible insertion section 28 extending from the grasping section. The insertion section 28 includes, as shown in FIG. 8, an image guide fiber 30 extending at the central area and a light guide fiber 32 concentrically arranged relative to the image guide fiber.

Figure 9:
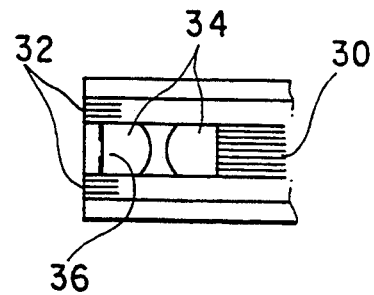
FIG. 9 is a longitudinal cross-section showing a distal end portion of the insertion section shown in FIG. 7.

The insertion section 28 has, at its distal end portion as shown in FIG. 9, an object optical system arranged in front of an entrance forward end face of the image guide fiber 30 and comprising a pair of object lenses 34 and a diaphragm 36. The aperture of the diaphragm 36 is fixed. The number of apertures of the object optical system is determined by F number of the object lens 34 and corresponds to the maximal number of apertures at the exit side of the object optical system.

The exit end face of the image guide fiber 30 is located at the eyepiece section on the operation section 22 of the endoscope 20. A TV camera 38 is detachably mounted on the eyepiece section of the endoscope 20. A focus adjusting/image size adjusting mechanism 40 and relay lens 42 are arranged at the TV camera, thus constituting an eyepiece optical system. Through the eyepiece optical system, an image at the exit end face of the image guide fiber 30 on the endoscope side is formed on the image receiving surface of a solid-state image pickup device 44. The image signal from the solid-state device 44 is converted to a video signal at a video signal processing circuit 46 and the video signal is transmitted to an observation monitor.

On the other hand, the operation section of the light guide fiber 32 is connected by a cable 50 to a connector 52 and hence detachably connected to a light source device 56 having a lamp 54.

In the system as set out above, the endoscope section is independently provided and properly used as a disposable one. Even in the case where a different region of interest is to be observed or a different intensity of light is required, a proper action can be taken against such a situation. Further, an action can also be taken under an improved specification on the TV camera 39 and light source device 56 simply by changing the associated individual component parts without modifying the system as a whole. It is, therefore, possible to obtain a very economic advantage.

The (maximal) numerical aperture (NA) at the entrance side of the relay optical system in the TV camera is 0.25 and the numerical aperture (NA) at the exit side of the object lens 34 is about 0.36 (F number: 1.4). An image guide fiber 30 is of such a multi-component type that it has a core diameter of 2 $\mu$m, 3000 pixels, numerical aperture of 0.5 and a length of 3.5 m. For a system for observing an object image using the eyepiece, not the relay lens system, it is only necessary to consider the numerical aperture (or F number) of the eyepiece instead of the numerical aperture (NA). In this case, it is only necessary to use, as F number of the eyepiece, a value which is involved when a light beam is back-tracked from the exit side to the entrance side. The numerical aperture at the entrance side has a relation given by the following equation (2):

$$F \text{ number of the eyepiece} = \frac{1}{2 \times NA \text{ at the entrance side}} \quad (2)$$

In this case, a variation in brightness of an image when F number of the object lens 34 of the endoscope 20 varies is indicated by a solid line in FIG. 10. From this it is found that an amount of light is increased even when F number of the object lens 34 is greater than F number of the relay lens in terms of their brightness.

When the numerical aperture (NA) ($\frac{1}{2}$ F number) on the exit side of the object lens is smaller than the numerical number (NA) of the fiber, the amount of light is increased at its increasing rate and, when the numerical aperture (NA) on the exit side of the object lens exceeds over the numerical aperture of the fiber, the amount of light is decreased at its increasing rate. When the numerical aperture on the exit side of the object lens exceeds the numerical aperture of the image guide, the degradation of the image becomes prominent due to a flare and cross-talk involved. It is, therefore, desirable that the numerical aperture on the exit side of the object lens be smaller than the numerical aperture of the image guide. Such an increase in the amount of light is prominent in a fiber having a standardized frequency v of a relatively small value and, particularly, a greater effect is obtained in a fiber having the v value of below 10. If, on the other hand, the V value becomes greater than that value, a resultant effect is decreased because it approaches the opto-geometric region. Here, the standardized frequency V is defined by the following equation (3).

$$V = \frac{2\pi}{\lambda} a \sqrt{n_1^2 - n_2^2} \quad (3)$$

where
λ: the wavelength
a: the core radius
$n_1$, $n_2$: the refractive indexes of the core and cladding, respectively.

Further, the image guide fiber 30 may be made up of a quartz-based image guide. In general, the quartz-based fiber is smaller in its numerical aperture than a multi-component-based fiber and, because of its high internal transmittance, a brighter image is readily obtained in a longer endoscope. The dotted line in FIG. 10 shows a brightness variation when F number of the object lens 34 varies with a quartz-based image guide of NA 0.35. In this case, when F number of the object lens 34 is above 1.4, there is a smaller brightness increase than in the multi-component-base image guide fiber 30. This is because the numerical aperture of the image guide fiber 30 is smaller than that of the multi-component-based one. It is to be noted that the difference in brightness between both when F number is small is ascribable to the difference in internal transmittance and core occupation ratio.

Although the image guide has been explained above, the same explanation can be applied to the light guide.

An explanation will now be made about the crosstalk.

It has generally been known that, when the core-to-core pitch becomes smaller in the image guide fiber, the cross-talk is produced. A cross-talk parameter B defined by the following equation (4) is known as a parameter representing such cross-talk.

$$B = |\beta_1 Z| \quad (4)$$
$$= |\{[-2u_{01}^2 K_0(w_{01}d/a)]/[V^2 K_1^2(w_{01})]\} \cdot Z/\beta|$$

where
$\beta_1$: the parameter of a fiber structure involved;
$u_{01}$, $w_{01}$: the eigenvalues of an $LP_{01}$ mode;
d: the core-to-core pitch;
a: the radius of the core;
z: the length of the image fiber;
$\beta$: the propagation constant of the $LP_{01}$; and
$K_m$: the m-order modified Bessel function of the second kind.

This is fully discussed in a paper entitled "transmission Characteristic of Image Fiber" in Transactions of the Institutes of Electronics and Communications Engineers of Japan, 83.11, vol. J66-C No. 11.

For the purpose of decreasing the cross-talk it may be said that the smaller the value of the cross-talk parameter B the better. Since, however, the brightness is decreased when the parameter B becomes smaller, the lower limit is restricted for a practical reason.

The cross-talk of the actual image fiber is smaller than that calculated from the cross-talk parameter of the above-mentioned equation. This is considered ascribable to the fact that, in the image fiber, there occurs a deviation from its designed value resulting from an error in manufacture (a variation in the diameter of fiber elements, a variation in the outer diameter of fibers upon spinning, etc.), a fluctuation in the refractive index, an internal residual stress, etc.

An explanation will be made about the experiments made by the inventors.

Four kinds of image fibers (samples I to IV) were prepared and tests were conducted for the cross-talk, noting that three kinds of light, that is, red (R), green (G) and blue (B) light, were used as measuring light.

Figure 11:
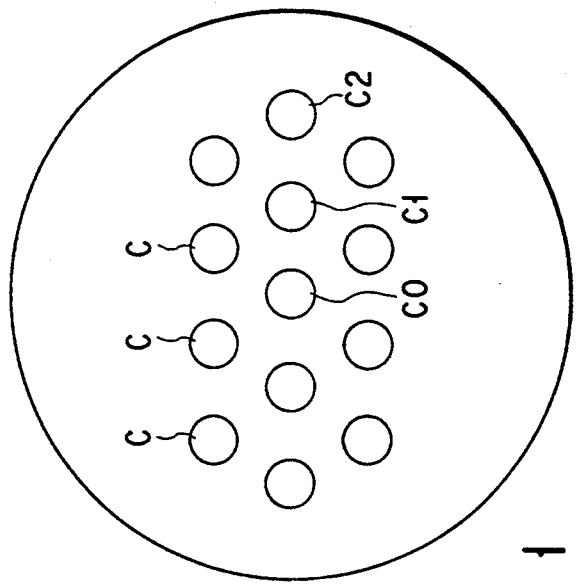
FIG. 11 shows an end face of an image guide fiber.
Figure 12:
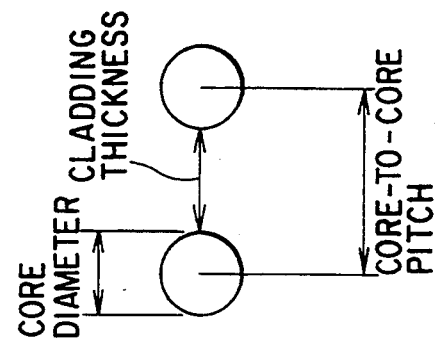
FIG. 12 shows a defined core diameter, core-to-core pitch and thickness of a cladding.

As shown in FIG. 11, each sample has a greater number of cores C in a common cladding as seen at its end face. These cores are so arranged in the cladding that, any three selected adjacent cores define an equilateral triangle when their centers are connected together.

Table 1 shows each of the specifications of four kinds of samples I to IV. The core diameter, core-to-core pitch and thickness of the cladding are as shown in Table 12. In this case, $n_1$ represents the refractive index and $n_2$, the refractive index of the cladding.

TABLE 1

| Sample | Core diameter (2a) | Core-to-core pitch (d) | Thickness of cladding (L) | Unit (μm) V value (λ-600) |
|---|---|---|---|---|
| I | 2.60 | 3.74 | 1.14 | 6.73 |
| II | 2.17 | 3.72 | 1.51 | 5.62 |
| III | 2.08 | 3.68 | 1.64 | 5.39 |
| IV | 2.12 | 3.81 | 1.69 | 5.49 |

$n_1 = 1.5963$
$n_2 = 1.5177$
$V1 = 54.2$
$V2 = 53.9$

Further, the cross-talk parameters B of these samples I to IV against the red light are as shown in Table 2.

TABLE 2

| | B value ($LP_{01}$ mode) | |
|---|---|---|
| | Length | |
| Sample | 1.5 m | 3.5 m |
| I | 39.71067 | 92.65823 |
| II | 11.825325 | 27.592425 |
| III | 7.286145 | 17.001005 |
| IV | 5.292435 | 12.349015 |

Of the cross-talk parameters B against three kinds of red, green and blue light, the cross-talk parameter B against the red light is the greatest and the cross-talk parameters against the green and blue light are smaller at all times than the cross-talk parameter against the red light. Upon evaluation for the degeneration of an image it is only necessary to evaluate the cross-talk parameter B against the red light. For such a reason, only the cross-talk parameter B is shown against the red light in Table 2.

Figure 13:
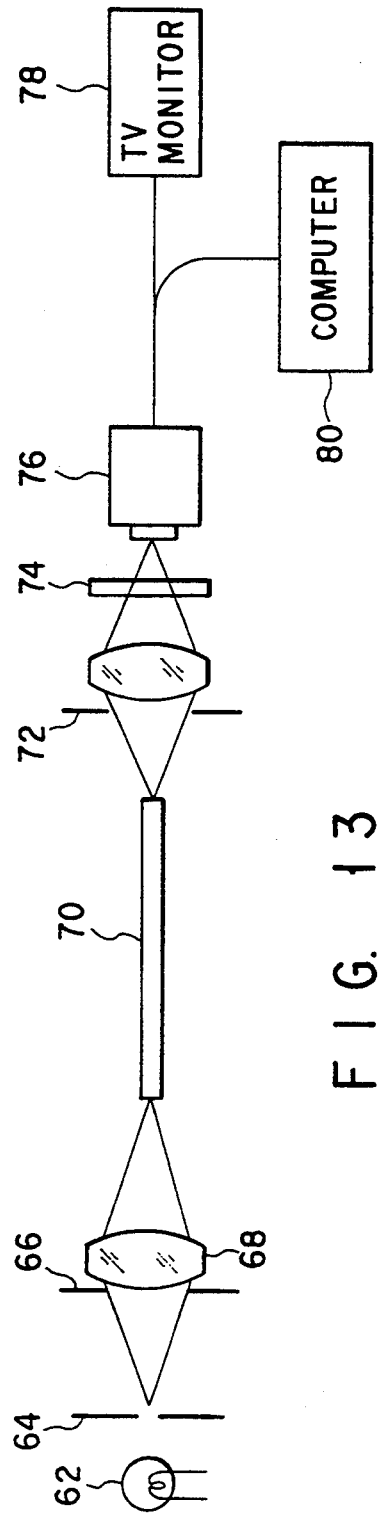
FIG. 13 shows an arrangement of an apparatus for measuring a cross-talk in the image guide fiber.

The measurement of the cross-talk was made with the use of an optical system having such an arrangement as shown in FIG. 13. A pinhole plate 64 is arranged in front of a lamp 62. The pinhole is regarded as a point source of light and light emerging from there is condensed with a lens 68 whose brightness diaphragm 66 is set to be F number=1.4 and is incident fully upon one of a greater number of cores in an image fiber 70.

An image formation lens 72 is arranged on an exit-end side of the image fiber 70 and an image on the exit-end face of the image fiber 70 is shot with a TV camera 76 after it has been passed through an image formation lens 72 and filter 74. That image information coming from the TV camera 76 is input to a computer 80 for 10 analysis to be done on the magnitude of the cross-talk, etc., and also to a TV monitor 78 where the image on the exit end face side is displayed.

Samples I to IV were prepared which had 1.5 m and 3.5 m in length, respectively. A xenon lamp was used as the lamp 12 and three kinds of filters were prepared which transmit red light (wavelength 600 nm), green light (wavelength 516 nm) and blue light (wavelength 476 nm). These filters were arranged as at 24 in figure and various measurements were carried out.

As will be understood from FIGS. 14 to 17, a cross-talk largely occurs with an increase in the wavelengths involved. It has been found that the greater the B value of the sample the smaller the ratio of the intensity of light staying in the center core (entrance core).

For the sample IV (1.5 m) having the smallest B value at the red wavelength (600 nm) for instance, the light intensity ratio of the center core is about 0.6. For the sample I (3.5 m) having the greatest B value, on the other hand, the corresponding ratio is about 0.2. It is readily estimated that, in an image fiber having a greater B value than these samples, there occur a further increase in cross-talk and a decrease in the light intensity of the center core and, in an image fiber having a smaller B value, on the other hand, there occur a decrease in cross-talk and an improvement in the light intensity ratio of the center core.

Figure 14:
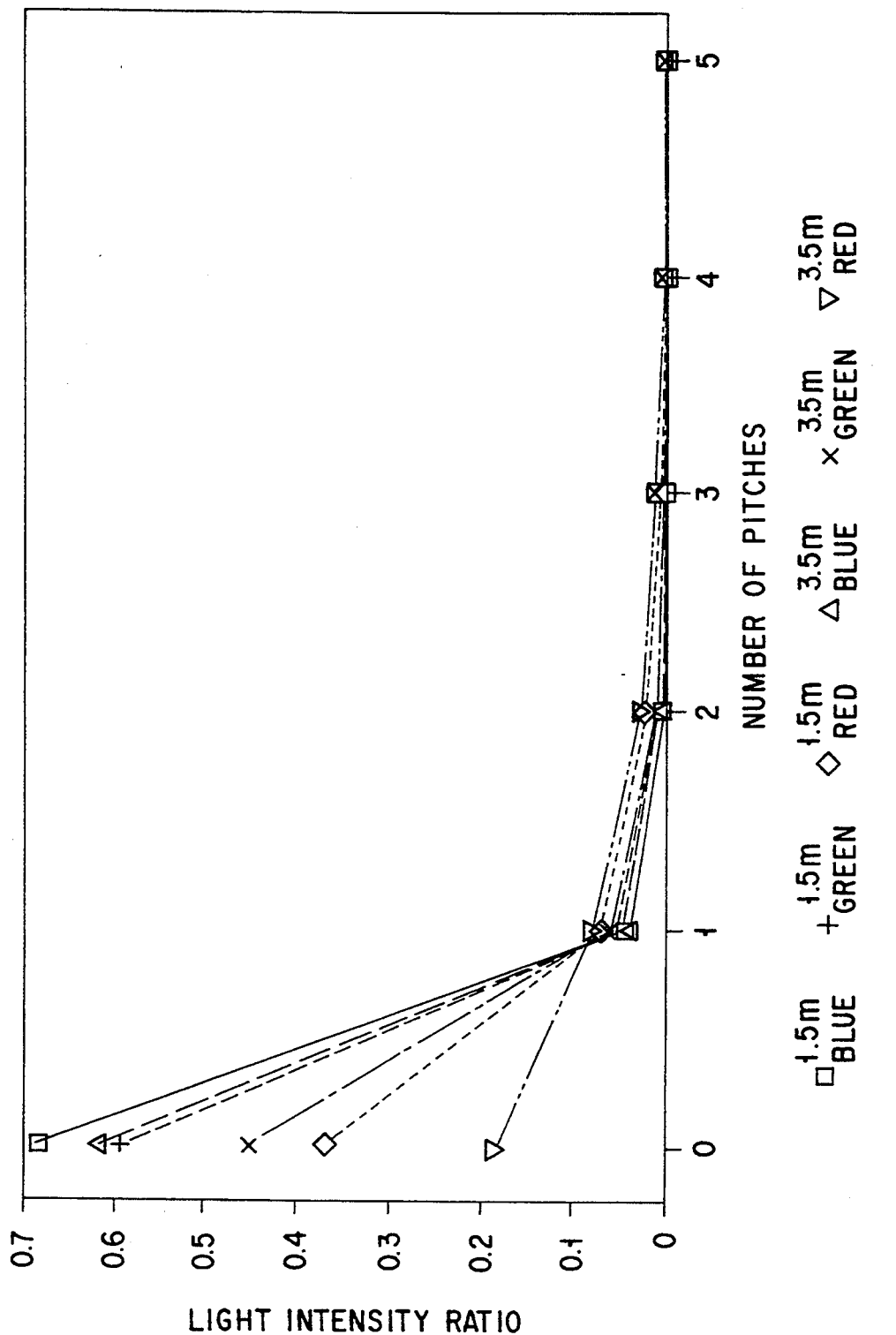
FIG. 14 is a graph showing a result of measurement of a sample I.
Figure 15:
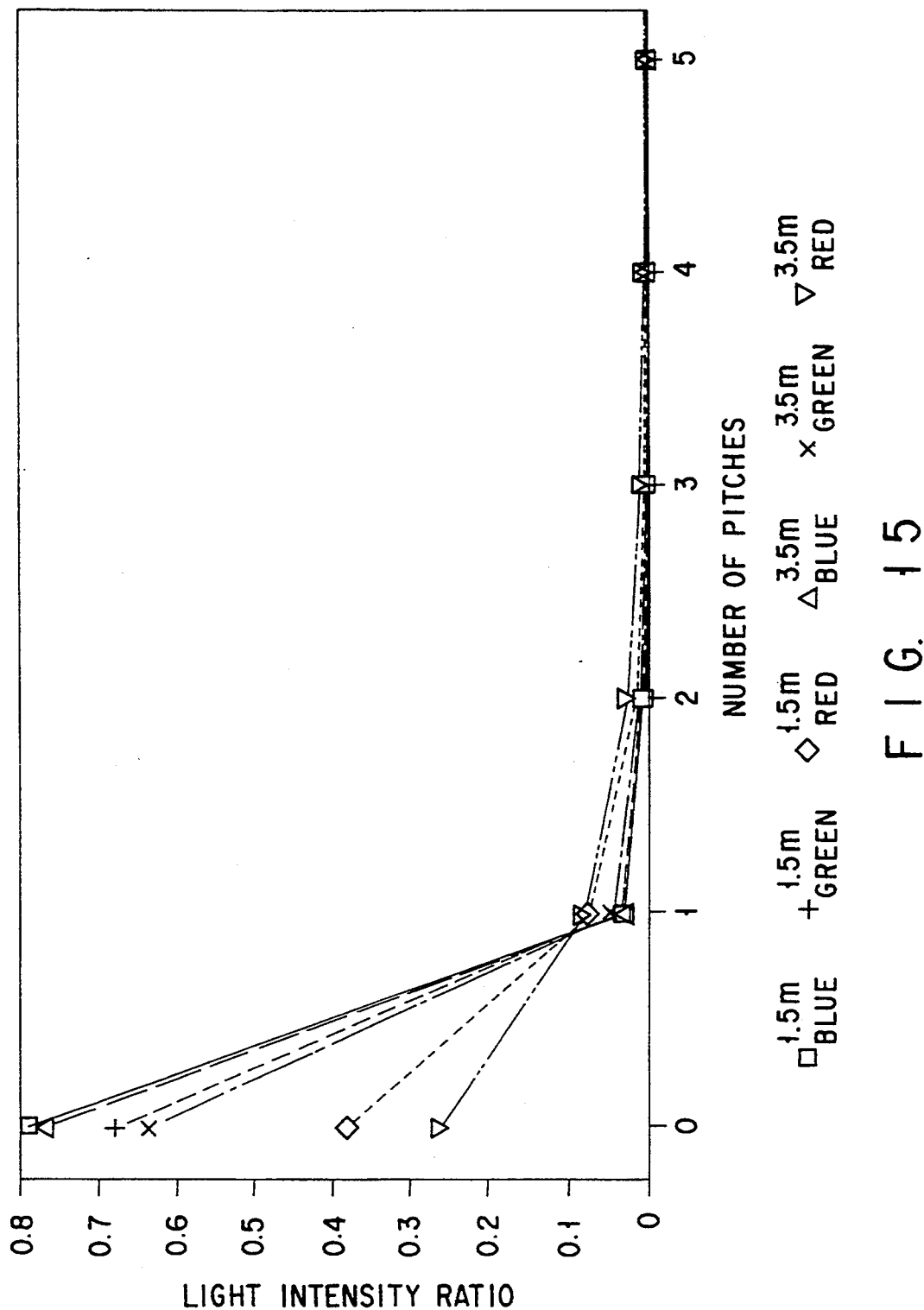
FIG. 15 is a graph showing a result of measurement of a sample II.
Figure 16:
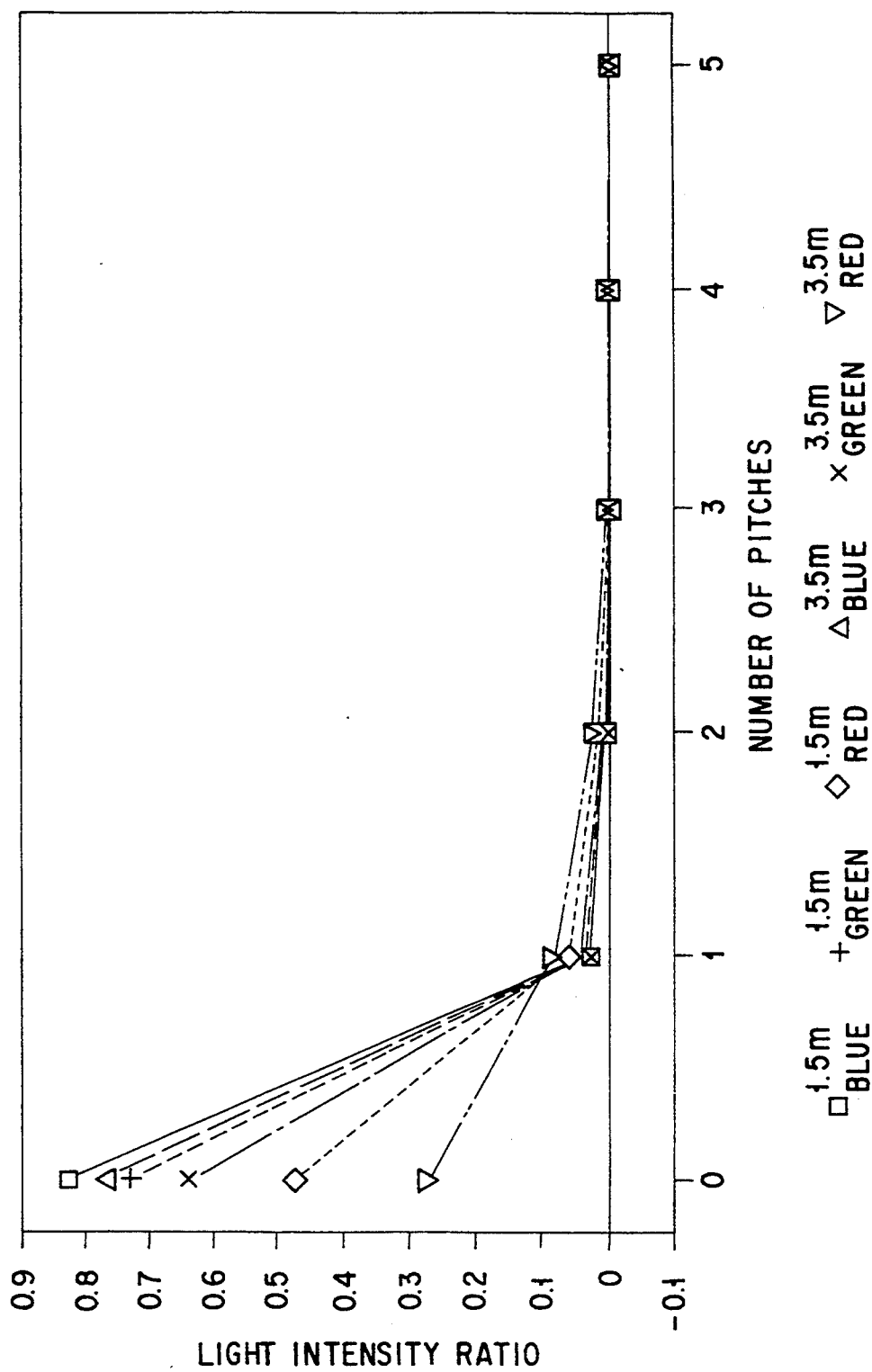
FIG. 16 is a graph showing a result of measurement of a sample III.
Figure 17:
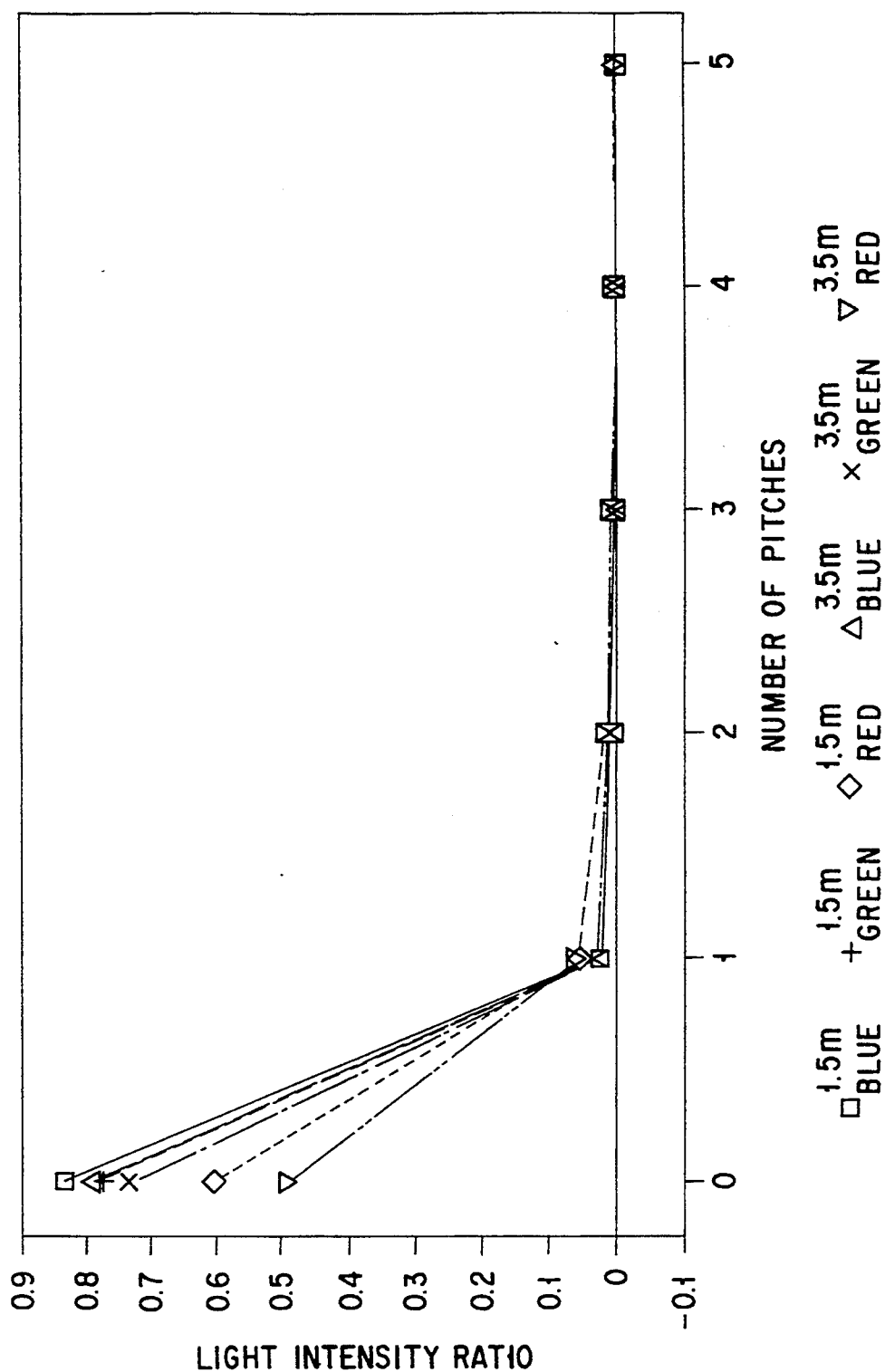
FIG. 17 is a graph showing a result of measurement of a sample IV.

FIGS. 14, 15 and 16 show a result of measurements for the samples I, II, III and IV. Tables 3, 4, 5 and 6 show their practical values, noting that the pitch number in these figures and Tables is counted in FIG. 11 like this: a light incident core Co is counted as O; the nearest core $C_1$ as 1; and the next nearest as 2.

TABLE 3

| Pitch number | 1.5 m Blue | 1.5 m Green | 1.5 m Red | 3.5 m Blue | 3.5 m Green | 3.5 m Red |
| --- | --- | --- | --- | --- | --- | --- |
| 0 | 0.68414 | 0.59242 | 0.36702 | 0.61622 | 0.45054 | 0.18115 |
| 1 | 0.03980 | 0.05125 | 0.06998 | 0.04642 | 0.05925 | 0.07866 |
| 2 | 0.00382 | 0.00762 | 0.02111 | 0.00407 | 0.00814 | 0.02268 |
| 3 | 0.00129 | 0.00147 | 0.00433 | 0.00078 | 0.00264 | 0.00958 |
| 4 | 0.00045 | 0.00043 | 0.00206 | 0.00007 | 0.00112 | 0.00291 |
| 5 | 0.00075 | 0.00138 | 0.00176 | 0.00584 |  | 0.00193 |

TABLE 4

| Pitch number | 1.5 m Blue | 1.5 m Green | 1.5 m Red | 3.5 m Blue | 3.5 m Green | 3.5 m Red |
| --- | --- | --- | --- | --- | --- | --- |
| 0 | 0.78676 | 0.67183 | 0.37509 | 0.77094 | 0.63232 | 0.25820 |
| 1 | 0.02764 | 0.04072 | 0.07370 | 0.03277 | 0.04570 | 0.07608 |
| 2 | 0.00226 | 0.00383 | 0.01267 | 0.00240 | 0.00488 | 0.01961 |
| 3 | 0.00038 | 0.00103 | 0.00276 | 0.00054 | 0.00122 | 0.00559 |
| 4 | 0.00038 | 0.00053 | 0.00083 | 0.00046 | 0.00062 | 0.00234 |
| 5 | 0.00002 | 0.00021 | 0.00053 | 0.00024 | 0.00016 | 0.00141 |

TABLE 5

| Pitch number | 1.5 m Blue | 1.5 m Green | 1.5 m Red | 3.5 m Blue | 3.5 m Green | 3.5 m Red |
| --- | --- | --- | --- | --- | --- | --- |
| 0 | 0.82374 | 0.72729 | 0.46954 | 0.76652 | 0.63459 | 0.26262 |
| 1 | 0.02233 | 0.03238 | 0.06048 | 0.02815 | 0.04152 | 0.07831 |
| 2 | 0.00177 | 0.00307 | 0.00944 | 0.00336 | 0.00487 | 0.01827 |
| 3 | 0.00081 | 0.00086 | 0.00179 | 0.00094 | 0.00113 | 0.00458 |
| 4 | 0.00054 | 0.00042 | 0.00061 | 0.00064 | 0.00034 | 0.00193 |
| 5 | −0.00038 | 0.00055 | 0.00061 | −0.00043 | 0.00096 | 0.00089 |

TABLE 6

| Pitch number | 1.5 m Blue | 1.5 m Green | 1.5 m Red | 3.5 m Blue | 3.5 m Green | 3.5 m Red |
| --- | --- | --- | --- | --- | --- | --- |
| 0 | 0.83150 | 0.77444 | 0.60067 | 0.79350 | 0.73198 | 0.48430 |
| 1 | 0.02062 | 0.02430 | 0.05464 | 0.02214 | 0.02805 | 0.05597 |
| 2 | 0.00217 | 0.00172 | 0.00668 | 0.00230 | 0.00275 | 0.00902 |
| 3 | 0.00100 | 0.00087 | 0.00084 | 0.00100 | 0.00096 | 0.00266 |

TABLE 6-continued

| Pitch number | 1.5 m Blue | 1.5 m Green | 1.5 m Red | 3.5 m Blue | 3.5 m Green | 3.5 m Red |
| --- | --- | --- | --- | --- | --- | --- |
| 4 | 0.00007 | 0.00117 | 0.00005 | 0.00034 | 0.00045 | 0.00131 |
| 5 | −0.00249 |  | 0.00168 |  |  |  |

Upon observing an image with a 3.5 m image fiber of the sample I, it has been found that the cross-talk involved is at a practical lower level but that adequate brightness is obtained. It has also been found that, for the 3.5 m image fiber of the sample IV, the brightness is somewhat inadequate but that a high contrast image is obtained with less cross-talk. From these experiments it has been concluded that, as a practical allowable range of the fiberscope, it is only necessary for the cross-talk parameter B to light (red light) of a wavelength 600 nm to satisfy the following equation:

$$200 > B > 0.7 \tag{5}$$

The upper limit of the equation shows a cross-talk limit and, when this value is exceeded, an image resolution is markedly degenerated. The lower limit shows a brightness limit and, for the samples I and IV in Table 1 for example, the core occupation ratio differs by 1.6 times. It is not possible to obtain adequate brightness at the cross-talk parameter B=below 0.7, taking into consideration the ingenious design, etc., of an illumination system.

Further, it is practically very desirable, taking into consideration a balance between the brightness and the cross-talk, that the cross-talk parameter B satisfy the following equation:

$$100 > B > 5 \tag{6}$$

In order to obtain an image fiber of high resolution it is required that the core pitch be made small. This necessarily decreases the core diameter. For example, the existing image fiber for an endoscope for blood vessels has an outer diameter of about 0.3 mm, a core diameter of 2 to 3 μm and a pixel number of about 3000. It is desirable for this type of image fiber to achieve a still high density version of pixels. In order to realize a pixel density of about 10000 it is necessary that the core diameter be reduced to about 1 μm. If the core diameter is so reduced, the V value becomes smaller, thus preventing a propagation mode limitation problem.

Here the V value represents the standardized frequency defined by the equation (3). The equation, again represented, is as follows:

$$V = \frac{2\pi}{\lambda} a \sqrt{n_1^2 - n_2^2} \tag{3}$$

where
   λ: the wavelength of light;
   a: the core radius; and
   $n_1$, $n_2$: the refractive indexes of the core and cladding, respectively.

Figure 18:
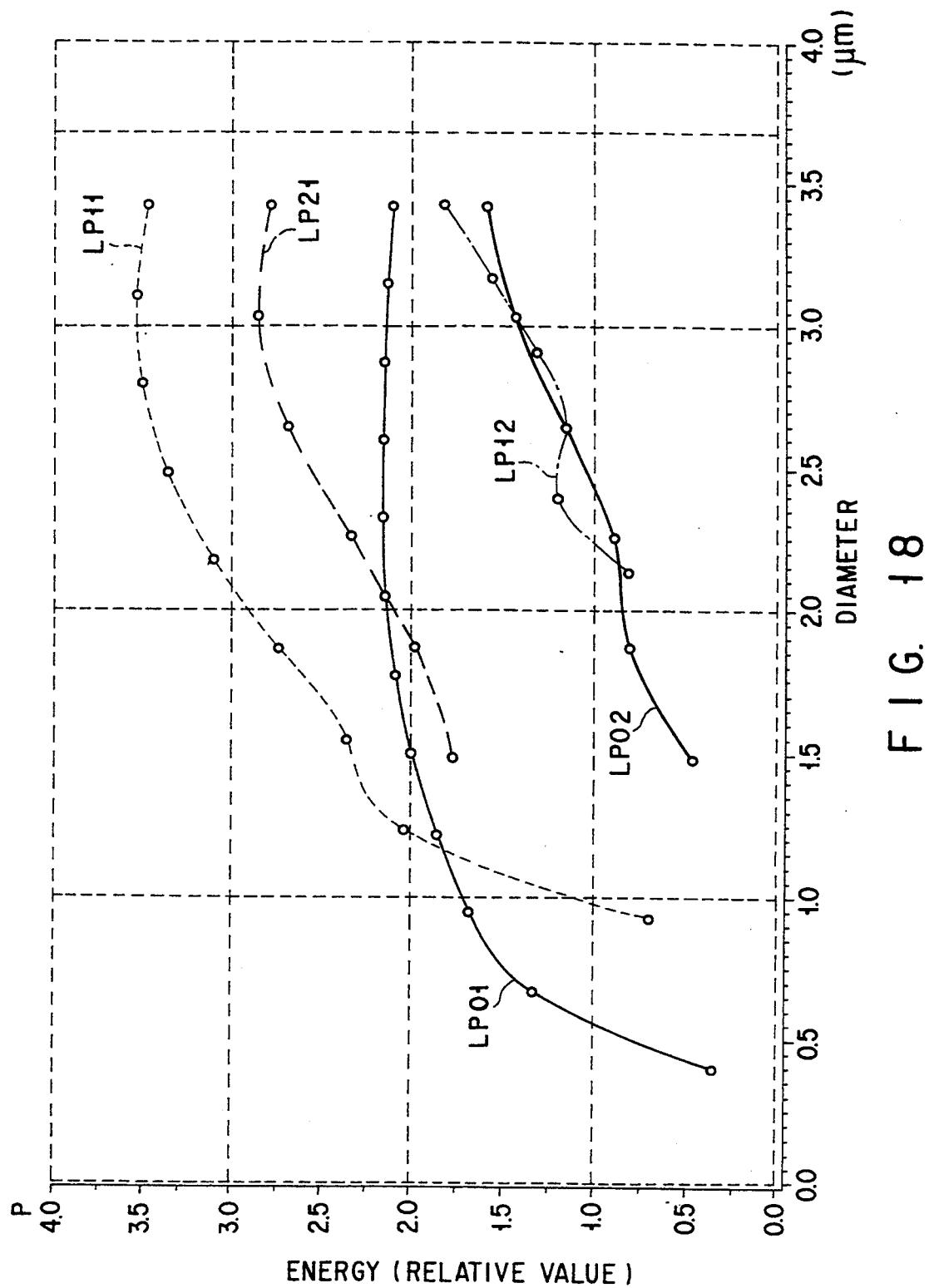
FIG. 18 is a graph showing an energy ratio of modes excited when light is incident on the optical fiber.

FIG. 18 is a graph showing an energy ratio of a mode excited when light (entrance F number: 1:4) is incident on an optical fiber of NA (numerical aperture)=about 0.5. In the graph of FIG. 18, the abscissa represents the core diameter and the ordinate, an energy involved. As appreciated from the graph, when the core diameter is decreased, $LP_{11}$ and $LP_{12}$ mode light of greater energy are not excited, thus causing darkening in the optical fiber.

In order to obtain brightness, it is desirable that the V value satisfy the following equation to excite at least the $LP_{11}$ mode.

$$V > 2.405 \tag{7}$$

If the V value satisfies the following equation, the $LP_{21}$ mode is excited to obtain a more desirable state.

$$V > 3.83 \tag{8}$$

In order to satisfy the equation (8) at the core diameter = 3 μm, then it is necessary that NA satisfy the following equation:

$$\sqrt{n_1^2 - n_2^2} > 0.24 \tag{9}$$

In order to satisfy the equation (8) at the core diameter = 1 μm, it is required that NA satisfy the following equation:

$$\sqrt{n_1^2 - n_2^2} > 0.73 \tag{10}$$

In the case where the image fiber is several tens of cm in length, the condition above can be realized, with ordinary optical glass, due to less transmittance loss, but, in the case of an image fiber of several meters in length it is necessary to have a high transmittance.

In the ordinary glass, an increase in the index of refraction leads to a decrease in transmittance. It becomes difficult, however, to satisfy the equation (10). The condition, using the equation (7), is as follows:

$$\sqrt{n_1^2 - n_2^2} > 0.46 \tag{11}$$

By satisfying these conditions and equation (4) it is possible to realize an image guide of more brightness and less cross-talk.

The refractive index of a multi-component-based glass is normally about 1.47 to 1.53 if the glass has a lower refractive index. It is required that the refractive index of the core material be at least over 1.54.

For the image fiber, the thicker the cladding, the less the cross-talk and, hence, it is possible to obtain a high-contrast image, but the brightness involved is decreased due to a decrease in the core occupation area. In order to secure practically adequate brightness, at least about 20% core occupation ratio is required and about 30 to 40% is preferable. An image fiber for use in endoscopes, etc., is, generally, about several tens of cm to 5 m in length. In order to satisfy the above occupation ratio in the range above and suppress the cross-talk to a practically allowable level, the thickness t of the cladding desirably satisfies the following equation.

$$1.8\ \mu m > t > 1\ \mu m \tag{12}$$

From experiments conducted it has been found that, for the core diameter of about 2 μm, the following range given by an equation (13).

$$1.7\ \mu m > t > 1.4\ \mu m \tag{13}$$

is particularly desirable.

A method for further decreasing the cross-talk of the image fiber will be explained below. In the state in which a cross-talk occurs, for example, light incident upon one core leaks from the exit end face of another adjacent core and, if the intensity pattern on the exit end side is to be seen, a high-order mode pattern can be observed at a core spaced-apart from the core upon which original light has been incident. From this it has been found that the cross-talk is decreased if such a high-order mode is shut off. For an image fiber having a partially narrow core diameter as shown, for example, in FIG. 19, the high-order mode is shut off at the narrow area of the core diameter, thus allowing propagation of only low-order light of less cross-talk.

Even if there occurs an internal residual stress by another means, for example, by partially cooling an image fiber at a spinning step during manufacture, the mode pattern varies, thus reducing a cross-talk involved.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An observation system for an endoscope having a very small-diameter image guide fiber, comprising:
    an image guide fiber including a plurality of cores and a common cladding to allow an image to be transmitted, the image guide fiber having an entrance end face upon which an image is incident and an exit end face from which the image exits;
    an object optical system arranged in front of the entrance end face of the image guide fiber; and
    a reproduction optical system arranged at a back side of the exit end face of the image guide fiber,
    wherein a maximal exit numerical aperture of the object optical system is greater than a maximal entrance numerical aperture of the reproduction optical system.

2. The observation system according to claim 1, wherein a standardized frequency V of the image guide fiber defined by an equation $$V = \frac{2\pi}{\lambda} a \sqrt{n_1^2 - n_2^2}$$

is below 10,
where
    λ: wavelength of light;
    a: core radius;
    $n_1$: refractive index of the core; and
    $n_2$: refractive index of the cladding.

3. The observation system according to claim 1, wherein the maximal exit numerical aperture of the object optical system is smaller than the numerical aperture of the image guide fiber.

4. The observation system according to claim 2, wherein the maximal exit numerical aperture of the object optical system is smaller than the numerical aperture of the image guide fiber.

5. An image guide fiber having a plurality of cores and a common cladding and having a cross-talk parameter B satisfying an equation given by:

$$200 > B > 0.7$$

where $$B = [\{-2u_{01}^2 K_0(w_{01}d/a)\}/[V^2 K_1^2(w_{01})]\} \cdot Z/\beta$$

and $U_{01}, W_{01}$: eigenvalues of $LP_{01}$ mode;
d: core pitch;
a: core radius;
Z: length of the image fiber;
$\beta$: propagation constant of $LP_{01}$;
$K_m$: m-order modified Bessel function of the second kind.

6. The image guide fiber according to claim 5, wherein the cross-talk parameter B satisfies the following equation $$100 > B > 5.$$

7. An image guide fiber having a plurality of cores and a common cladding and having a standardized frequency V satisfying an equation $$V > 2.405$$

where $$V = \frac{2\pi}{\lambda} a \sqrt{n_1^2 - n_2^2}$$

and $\lambda$: wavelength of light;
a: core radius;
$n_1$: refractive index of the core; and
$n_2$: refractive index of the cladding.

8. The image data fiber according to claim 7, wherein the image guide fiber has a numerical aperture which satisfies the following equation $$\sqrt{n_1^2 - n_2^2} > 0.46.$$

9. The image guide fiber according to claim 7, wherein the standardized frequency V satisfies the following equation $$V > 3.83.$$

10. The image guide fiber according to claim 9, wherein the image guide fiber has a numerical aperture which satisfies the following equation $$\sqrt{n_1^2 - n_2^2} > 0.24.$$

11. The image guide fiber according to claim 10, wherein the image guide fiber has a numerical aperture which satisfies the following equation $$\sqrt{n_1^2 - n_2^2} > 0.73.$$

12. An image guide fiber having a plurality of cores and a common cladding, a cladding thickness t being defined by a minimal distance between the adjacent cores and satisfying the following equation $$1.8 \ \mu m > t > 1 \ \mu m.$$

13. The image guide fiber according to claim 12, wherein the cladding thickness t satisfies the following equation $$1.7 \ \mu m > t > 1.4 \ \mu m.$$

* * * * *